United States Patent
Krieftewirth

(10) Patent No.: US 9,014,986 B2
(45) Date of Patent: Apr. 21, 2015

(54) METHOD FOR STORING A SERIES OF MEASUREMENTS

(75) Inventor: Michael Krieftewirth, Ersigen (CH)

(73) Assignee: Roche Diagnostics International AG, Rotkreuz (CH)

( * ) Notice: Subject to any disclaimer, the term of this patent is extended or adjusted under 35 U.S.C. 154(b) by 1261 days.

(21) Appl. No.: 12/760,808

(22) Filed: Apr. 15, 2010

(65) Prior Publication Data

US 2011/0106453 A1    May 5, 2011

Related U.S. Application Data

(63) Continuation of application No. PCT/EP2008/008692, filed on Oct. 15, 2008.

(30) Foreign Application Priority Data

Oct. 16, 2007 (EP) .................................. 07405308

(51) Int. Cl.
- *G01N 33/48* (2006.01)
- *G01D 9/00* (2006.01)
- *A61B 5/00* (2006.01)
- *A61B 5/145* (2006.01)

(52) U.S. Cl.
CPC .............. *G01D 9/005* (2013.01); *A61B 5/0002* (2013.01); *A61B 5/14532* (2013.01)

(58) Field of Classification Search
USPC .......................................................... 702/19
See application file for complete search history.

(56) References Cited

U.S. PATENT DOCUMENTS

| | | |
|---|---|---|
| 5,840,020 A | 11/1998 | Heinonen et al. |
| 2002/0161288 A1 | 10/2002 | Shin et al. |
| 2003/0100040 A1 | 5/2003 | Bonnecaze et al. |
| 2003/0235817 A1 | 12/2003 | Bartkowiak et al. |
| 2005/0038332 A1 | 2/2005 | Saidara et al. |

FOREIGN PATENT DOCUMENTS

| | | |
|---|---|---|
| GB | 2393356 A | 3/2004 |
| WO | 2005/041103 A2 | 5/2005 |
| WO | 2005/065542 A2 | 7/2005 |
| WO | 2007/116226 A2 | 10/2007 |

OTHER PUBLICATIONS

Hovorka, Roman et al., "Nonlinear model predictive control of glucose concentration in subject with type 1 diabetes", Physiological Measurement, No. 25, pp. 905-920 (2004).

Hann, Christopher et al., "Integral-based parameter identification for long-term dynamic verification of a glucose—insulin system model", Computer Methods and Programs in Biomedicine, No. 77, pp. 259-270 (2005).

*Primary Examiner* — Jerry Lin
(74) *Attorney, Agent, or Firm* — Dinsmore & Shohl LLP

(57) ABSTRACT

A method reducing storage volume of a series of measured time-dependent parameters measured in or on the human body such as glucose values from a continuous glucose monitor while permitting retrospective reconstruction of measured data with sufficient accuracy. The series comprises a first number of measured values, and a second number of values that are stored. In this case, the second number is smaller than the first number. A first storage mode is provided, in which an interval of time between successive stored values is variable and which is adjusted on the basis of a time-based variability of the measured values. A second storage mode may also be provided, in which the interval, of time between successive stored values is constant. Embodiments of the invention include a measuring apparatus and a computer program.

23 Claims, 4 Drawing Sheets

US 9,014,986 B2

METHOD FOR STORING A SERIES OF MEASUREMENTS

REFERENCE

This application is a continuation of PCT/EP 2008/008692 filed Oct. 15, 2008 which is based on and claims priority to European Patent Application. No. EP 07405308.3 filed Oct. 16, 2007, which are hereby incorporated by reference.

FIELD

The disclosure relates to a method for storing a series of measured values which represent a time-dependent parameter measured in or on the human body such as a physiological glucose concentration. The disclosure also relates to an apparatus and a computer program product for carrying out the method.

BACKGROUND

The body of a person suffering from diabetes is not able to produce a sufficient quantity of insulin, or it does not react in an appropriate way to the insulin it produces. This fact results in an imbalance in the glucose concentration in the blood (that is to say in hyperglycaemia or hypoglycaemia) which may be the cause of serious consequences, such as ketoacidosis, complications in the blood vessels, spasms or loss of consciousness. To maintain a healthy blood glucose level (also known as blood sugar level), diabetic patients usually follow strict diets and combine these with a basal insulin release and with selective insulin boluses. In this case, the insulin release needs to be individually tailored to the patient's body in order to provide it with the correct amount of insulin at the correct time. To determine the time and amount of the next insulin bolus, patients regularly measure the glucose concentration in their blood and determine the carbohydrate content of their meals.

Instead of taking blood glucose measurements using strip meters, which, depending on the intensity of the therapy being carried out, happens three to six and only in exceptional cases, ten or more times per day, it is possible to use continuously operating blood glucose meters. One of the advantages of a continuously operating measurement system is the facility to calculate trend information, which can only be done usefully with a high rate of measured data. In this case, the calculated trend information usually relates to the values measured beforehand and therefore provides information about the profile of the glucose concentration in the near future. External influences such as the administration of an insulin bolus, the taking of meals or sports activities influence the accuracy of the trend information. Supplying a measurement system with information about these external influences can significantly increase the accuracy of the trend calculation and therefore particularly also allows the dosage of an insulin bolus to be matched more accurately to the needs of a patient.

Blood glucose meters for continuously collecting glucose data are usually portable. Data stores for storing the captured data account for a significant proportion of the appliance costs in the case of such appliances. With the currently usual sampling intervals of five minutes, for example, a large volume of data is already produced which cannot be effectively compressed using conventional data compression without losing valuable information. In addition, by way of example, retrospective trend calculation with sufficient accuracy for the further data evaluation is possible only with difficulty, even at five-minute storage intervals, particularly if the stored signal is additionally overlaid with noise.

SUMMARY

One aspect of the invention to provide a method associated with the technical field cited at the outset which allows the stored volume of data to be reduced, wherein retrospective reconstruction of the measured values is possible with sufficient accuracy.

Another aspect of the invention provides a method for storing a series of measured values which represent a time-dependent parameter measured in or on the human body. In line with this aspect of the invention, the series comprises a first number of measured values, wherein a second number of values is stored, the second number being smaller than the first number.

In this case, the measured parameters may be already interpreted and ascertained or derived values, e.g. absolute values for the glucose concentration, or else partially processed data and/or raw data, such as voltage or current values, which are output directly by appropriate measurement sensors. Subsequently, a "continuously" ascertained series of measurements is understood here and below to mean measured data acquisition which takes place quasi-continuously using a certain measurement period, particularly one which is short in comparison with the variability of the actual time profile of the measured parameter. The measurement period is chosen to be small enough for it to be able to be assumed that the actual profile of the measured parameter is largely reproduced by the series of measurements. Typical measurement periods are from a few seconds to a few minutes. In this case "continuous" measurements are particularly contrasted with known blood glucose measurements using strip meters, for example, which are taken three to six and only in exceptional cases ten or more times per day, depending on the intensity of the therapy being carried out.

Not every measured value in the series of measurements has the same relevance for later, retrospective reconstruction of the series of measurements with sufficient accuracy. To be able to reconstruct the time profile of the series of measurements, it is accordingly sufficient to store a smaller number of values than has been measured. Measured values which are assessed as being less relevant or as being irrelevant to the profile of the measurement curve on the basis of prescribed criteria and/or criteria which need to be determined from the measured data are singled out and not stored. Such, incomplete or partial storage of measured values, from the continuous series of measurements means that the number of stored values is smaller than the number of measured values; and the stored total volume of data for the series of measurements (i.e. for the continuously recorded glucose values) is therefore reduced. In this case, it is entirely possible for it also to be advantageous to store additional values, for examples values derived from the measured values, but in line with the invention the number of values to be stored in total is smaller than the number of measured values in this case too.

Whether a measurement point is relevant to the curve profile and hence needs to be stored can be ascertained on the basis of a storage criterion associated with the measured value. Possible storage criteria may be firmly prescribed, for example, and based on an a priori known time-based variability of the measurement curve. On the basis of the previously known variability, it is possible to establish the interval of time or the storage interval at which measured values need to be stored, for example, so that retrospective reproduction of the measurement curve with sufficient accuracy is assured.

Depending on the measurement period, it is sufficient to store only every nth measured value, for example, wherein n is also dependent on the variability of the measured values, for example.

Other storage criteria are based on analyses of the measured values or values derived therefrom and/or on further, additional ascertained data and result in variable storage intervals, for example. Such storage criteria can be continually adjusted on the basis of the measured values and/or further ascertained parameters or are recalculated and reevaluated for every new measured value, for example.

One option for an adaptive storage criterion for a measured value involves ascertaining a discrepancy or an error value for most recently measured values from a prediction or extrapolation from the stored values, for example. If the discrepancy exceeds a certain extent, it can be inferred from this that it is necessary to store a further measured value. In this case, for example, only a most recently measured value can be compared with the prediction or else a series of current measured values. In particular, selection criteria can also be derived from a plurality of measured values, available to the portable appliance, in the series of measurements. In this case, brief buffer-storage in a buffer or buffer store, for example, ensures access to the continuous measured values in a prescribable time window, or one matching requirements, of a certain duration. In particular, all the measured values in the buffer store can be used for filtering and/or for sufficiently accurate calculation of, by way of example, trends, (e.g. first derivative of the measured value with respect to time) or other parameters based on the profile of series of measurements (e.g. higher derivatives with respect to time, variance in the measured data in a time window, extrapolation, etc.).

A storage interval or a storage criterion can preferably also be chosen or adjusted such that fluctuations on a certain time scale can be filtered out (in this regard, see Nyquist criterion, for example). In particular, a storage interval can be adjusted such that although the complete physiological curve profile can essentially be restored retrospectively, noise and/or other appliance-related short-term measurement inaccuracies is/are filtered out. Such selection of the measured values to be stored is used for filtering in the sense of a low-pass filter, and this smoothes a measurement curve which is to be reconstructed later.

Finally, a storage interval or storage criterion can also be ascertained using additional information on events which influence the measured parameter, for example. By way of example, if the measured parameter is a glucose concentration in a person's blood, it is also possible to include the nature, time or, by way of example; the carbohydrate content of meals taken, administered insulin boluses or the nature and duration of an undertaken sports activity.

To ensure that a measurement curve which can be reconstructed from the stored values is better matched to the profile of the continuous series of measurements, one variant of the method provides a first storage mode, in which an interval of time between successive stored values is variable. The effect achieved by this is that storage intervals for the measured values, i.e. the time intervals between two stored values, can be matched to requirements.

By way of example, variants of the method comprise different storage intervals, but ones which are firmly prescribed on the basis of a time of day or specific phases, for example. In this case, in periods of low dynamics, such as in the fasting state or during the night, longer storage intervals can be prescribed, whereas shorter storage intervals can be prescribed in phases of the day with relatively high dynamics. The storage intervals can be firmly prescribed such that the originally measured values can be reproduced by the stored values, with a sufficiently high level of accuracy.

In the first storage mode the interval of time between the stored values can be adjusted on the basis of a time-based variability of the measured values. In this case, the method is adaptive such that, by way of example, a measured value is stored comparatively rarely in periods of low dynamics and measured values are stored comparatively often in periods of high dynamics, in particular automatically. A variability analysis can be performed on the basis of the continuous measured values buffer-stored in the buffer store. The variability analysis allows a time to be stipulated for the next storage of a measured value, for example. Alternatively, the variability analysis can be taken as a basis for ascertaining a storage criterion which, by way of example, is assigned to an already measured value in the buffer store, e.g. a most recently measured value; and whose evaluation determines storage of the associated value. Such adaptive adjustment of the storage'intervals can be taken as a basis for further reducing a volume of data which is required for sufficiently good reconstruction of the curve.

In one variant of the method, a measure of error is formed from an interpolation between a last stored value and a most recently measured value for a relevant range of the series of measured values. In this case, a measured value for the relevant range of the series is stored if the measure of error exceeds a certain maximum value. The measure of error thus results in a storage criterion for a measured value in the relevant range of the series, i.e. in a range of the series between a most recently stored value and a most recently measured value. In particular, the interpolated range also comprises a most recently measured value which, in one possible variant of the method, is stored on the basis of a maximum value of the measure of error being exceeded.

In other words, the time profile of the measured parameter is interpolated in a time period between the time of a most recently stored value and the time of a most recently measured value. The continuous values buffer-stored in the buffer in this time period are compared with the interpolation and a measure of error is determined from the interval between the interpolated profile and the actual profile. In this case, by way of example, the (normalized) largest discrepancy in the two curves or a (normalized) area between the two curves in the given time period can be used as a measure of error. In principle, however, all measures known from measure theory, for example, which allow an interval between two curves in a prescribed range to be quantified in some way are also suitable for this.

If the measure of error exceeds a certain prescribable or firmly prescribed tolerance value or maximum value, the storage criterion for the most recently measured value is deemed to have been met. In other words, the measure of error can establish whether a new measured value needs to be stored so that a prescribed tolerance or discrepancy is not exceeded during later reconstruction of the measurement curve. Depending on the variant of the method, however, it may also be advantageous to store not a most recently measured value'but rather, by way of example, a value measured before the last value in the buffer store, particularly a value measured as the penultimate, when the maximum value is exceeded, since at this measured value the measure of error has not been exceeded.

On the basis of the interpolation, this aspect of the invention therefore allows a prediction of the measured value profile on the basis of earlier stored values and/or continuous measured values stored in a buffer store also to be included in the selection of the values to be stored. By way of example, the interpolation can be influenced by means of a weighting for the measured values stored in the buffer, for example by virtue of older values being assigned a lower weight than more recent and more current values.

In one variant of the method, the interpolation is effected as a linear interpolation for the time period between the time of a last stored value and the time of the most recently measured value. A linear interpolation method requires only a low level of computation complexity and therefore achieves a high speed. This means that only comparatively sparse resources need to be provided for the interpolation. To determine the measure of error as a basic criterion for selection of measured values for storage, the accuracy achieved with linear interpolation is sufficient for most requirements. However, it is entirely possible for preference also to be shown for variants of the method which make use of higher-order interpolation methods in order to achieve better accuracy. The way in which the interpolation method is chosen is essentially dependent upon how the measure of error or its maximum value is defined and how the measurement curve is later reconstructed from the stored values. On account of the relatively few resources required and the extremely good accuracy, however, a linear method can be helpful if it can be used.

To be able to optimize the adjustment of the storage interval further, one variant of the method provides a second storage mode, in which the interval of time between successive stored values is constant. In this case, particularly the first storage mode is used if a variability of the measured values is below a prescribed value, and the second storage mode is used if the variability of the measured values exceeds the prescribed value.

With high variability, continual analysis and adaptive adjustment of the storage intervals can result in a high level of computation complexity, which may be undesirable. In this case, it is therefore sometimes advantageous to keep the storage interval constant and to dispense with continual analysis prior to any storage of a value. In this case, the storage intervals need to be stipulated to be sufficiently short to ensure good sampling of the measurement curve, by the stored values. The variability of the measurement curve can be analyzed sporadically, for example, in the first storage mode in order to change over automatically to the second storage mode if appropriate, for example in the case of relatively low variability. In the second storage mode, intervals of time between two successive stored values can be extended to periods in which the low variability does not require a measured value to be stored again. Changeover between the two storage modes can be effected automatically on the basis of a variability analysis, but may also be effected manually, for example if increased dynamics are expected at an unexpected time of day (e.g. unexpected night activity).

Variants of the method which allow operation in only one of the two storage modes can be used depending on requirements. With a view to the greatest possible flexibility in matching the storage method to a profile of the measurement curve, the method can have an embodiment with both storage modes.

The method is not limited to storage or analysis of measured values, however. In order to obtain additional information relating to the profile of the measurement curve, it is also possible to ascertain derived variables from the measured values. In particular, previously measured values can be used to obtain trend information, for example, which provides an estimation of the further profile of the measurement curve, i.e. of the glucose concentration in the near future. In one variant of the method, trend values are therefore ascertained from the series of measured values. In this case, possible trend values comprise a first derivative on the basis of the time of the measured values, for example.

The ascertained trend values can be taken as a basis for significantly improving or simplifying the predictive value of the further measurement curve profile on the basis of buffer-stored measured values, for example. In particular, the inclusion of trend information allows improvement or simplification of a prediction when interpolating to determine the measure of error.

The trend values or the measure of error can be ascertained using a Kalman filter, a known state estimator for discrete-time systems. The Kalman filter is used particularly for estimating states or parameters of the system on the basis of partially redundant measurements which are overlaid with noise, In this case, the mean square error is minimized. The Kalman filter is an adaptive filter, which means that the relevant values are continually improved and a good estimate of the trend or of the measure of error is always available.

To simplify or improve later reconstruction of the measurement curve from the stored data and/or particularly to obtain the volume of data to be stored given constant reproducibility of the measurement curve, trend values can be stored besides the stored values. By way of example, the trend values can be stored with the selected values as a simultaneous pair of values. Alternatively, trend values can be stored in a storage interval between the storage of two successive values. In particular, trend determination is difficult with large storage intervals for the stored measured values, which is why additional storage of the trend values improves the reconstructability of the measurement curve on the basis of the stored values.

In this variant of the method, although further values are stored besides the measured values, the additional trend information means that the next storage may not be required until after a comparatively long period, as a result of which the volume of data to be stored for reconstructing the measurement curve in a prescribed quality can be reduced further in total.

In one variant of the method, the current measured value is stored if a trend value change associated with the currently measured value exceeds a prescribed minimum value. In particular, a measured value is stored precisely when an absolute value for the first time-based derivative of the trend values exceeds a certain minimum value. When the minimum value for the trend change is exceeded by an absolute value, a pair of values can be stored which comprises the relevant measured value and an associated trend value.

In this case, the derivative can be ascertained at the time of measurement of the value which is to be stored, or at another time and can be associated with the value which is to be stored. By way of example, it is conceivable for the absolute value of derivative of the trend values with respect to time at the time of a most recently stored value to form a storage criterion for a current measured value.

Trend change values corresponding to a second derivative of the measured values with respect to time can be ascertained from the series of measured values. This is the case particularly when the first derivative with respect to time for the measured values is used for the trend values. In other words, in this case a measured value is stored if the absolute value of a second derivative with respect to time associated with it exceeds a prescribed minimum value. The trend change values can be used only for determining the storage criterion or can be stored in addition to the measured values and/or trend values.

A second variant of the method provides time-based interpolation points at which the relevant trend value and/or trend change value, but not the measured value itself, is stored. By way of example, it is conceivable for the trend value or the trend change value to be stored in the time interval between two stored values. In this case, the time at which the trend values are stored or a trend change value can be determined adaptively on the basis of the variability of the measurement curve, or may be firmly prescribed, for example for a period between two successive stored values, e.g. at the central point in time.

The effect achieved by the additional ascertainment and possibly the storage of trend values or trend change values for the selected measured values is that the storage method allows adjustment to suit a variable measurement curve in order to reduce or at best minimize the volume of data required for sufficiently accurate reconstruction of the measurement curve.

An apparatus for carrying out a method which can be described as above comprises a measuring apparatus for continuously measuring a series of measured values for a parameter measured on or in a human body, particularly for a glucose concentration. The apparatus also comprises a system controller having a memory unit for storing the measured values, wherein the system controller is in a form and programmed such that for a first number of the values covered by the series a second number of values can be stored, the second number being smaller than the first number.

The apparatus comprises all the aforementioned elements in order to be able to operate as a functional unit. At least the system controller needs to have or be able to address appropriate input and output apparatuses. It is not absolutely necessary for a measuring apparatus to be integrated in the apparatus. However, the measured values need to be supplied to the apparatus in a certain manner or need to be fed into it, which can also be done using an external measuring apparatus, for example. The same applies for the output of the data, which, admittedly, preferably makes use of a display contained in the apparatus; for example. In principle, however, it is sufficient for there to be an apparatus for transmitting data to an, in particular, external display appliance.

The entire apparatus can be integrated in a single appliance which is advantageously in portable form. In particular, the portable appliance is in a form such that a user is not or is only insignificantly restricted in his freedom of movement by the appliance. For the purpose of reading data or for the purpose of charging a battery, the appliance can be connected to a PC or to another base station, for example. In addition, the portable appliance may comprise display means such as a display and also control elements so as firstly to display measured data and stored values and secondly to allow input by a user. By way of example, the control element may allow changeover between the first storage mode and the second storage mode.

In particular, appliances for continuous glucose monitoring (CGM) are particularly suited to carrying out methods according to embodiment of the invention. CGM denotes a new technology for monitoring a diabetic disorder oneself. Such appliances are distinguished particularly by the fact that firstly a glucose concentration in the body is recorded over periods of between a few hours and a few days or even weeks and months. Secondly, the frequency of a measurement is much greater (range of minutes) than in the case of conventional blood glucose measurement methods (hours). The fact that these data with high time resolution are stored allows the patient and/or a person responsible for the health of the patient to use the data for adjusting a therapy and, if appropriate, to start adjusting eating, habits or medication etc. for the patient, for example. In addition, the storage allows a personal data archive to be created which, by way of example, allows long-term analysis of patient-specific metabolic reactions to certain events as sequences and forms or patterns with a high time resolution.

For measuring a glucose level, the apparatus can comprise a continuously operating glucose sensor which is arranged in or on the human body in order to measure a glucose concentration in body fluids. The measured values are stored in the apparatus or can be transmitted to other components for data processing or visual display of data, particularly to PDAs, PCs, mobile phones or remote controls for insulin pumps or to insulin pumps directly, for example. The sensor may also be integrated in analyzers, such as portable CGM appliances, or may be connected to such appliances, for example. Preferably, such analyzers also comprise a display, particularly a screen, on which current and stored data can be displayed. In particular, such appliances are preferably in a form of this kind or are provided with all the components which are required for carrying out methods.

To be able to buffer-store the values continuously measured by the measuring apparatus for intermediary access, the apparatus can comprise a buffer store. In this case, the buffer store is in the form such that other components of the apparatus can access it in order to be able to remove or feed in buffer-stored measured values when required. The buffer store may be directly integrated in the system controller, but can be integrated directly in the measuring apparatus. In particular, a buffer store of this kind is in a form such that a plurality of measured values can be stored which have been ascertained prior to a current time. The plurality of measured values in the buffer store therefore corresponds to a measured profile of the measurement curve in a time window before the current time. Buffer stores which are suitable for this purpose preferably operate on the basis of a first-in-first-out (FIFO) principle or on the basis of a bucket-chain principle. In the case of such memory architectures, those contents of the buffer store which have been stored first are also removed from the buffer store, or erased or overwritten, first.

In addition, an apparatus can comprise an evaluation apparatus which allows analysis, particularly of a variability, of the measured values. By way of example the evaluation apparatus removes buffer-stored measured values from the buffer and determines a current variability of the measurement curve on the basis of an analysis of the removed measured values and, if necessary, of current measured values. The analysis can then be taken as a basis for the system controller to extrapolate or estimate a further profile for the measurement curve, for example, and/or to adjust a period up until the next storage of a measured value.

In addition, the system controllers can comprise a computer for calculating trend values using the expected future profile of the measured parameter. In one embodiment, the computer is also in a form and programmed such that derivative of the measured values with respect to time can be calculated. The computer can be in the form and programmed such that it is also possible for a second time-based derivative of the measured values with respect to time, i.e. a first derivative of the trend values with respect to time, to be calculated. In this case, the computer interacts with the other components of the apparatus, particularly such that the derivatives of the measured values can be stored when required.

One of the aforementioned methods can be carried out using a computer program product which processes data from a parameter measurement performed continuously on or in a human body, the measured parameter being able to describe a glucose concentration in particular. The computer program is particularly suited to execution on a data processing apparatus. This may be a commercially available laptop, in particular, to which a measuring apparatus as described above is connected, or the computer program can be executed on a portable appliance provided specifically for this purpose.

Further embodiments and combinations of features of the invention can be found in the detailed description below and in all of the patent claims.

BRIEF DESCRIPTION OF THE DRAWINGS

The drawings used to explain the exemplary embodiment are schematic illustrations, in which.

As a general rule, identical parts have been provided with the same reference symbols in the FIGS.

DETAILED DESCRIPTION

Figure 1:
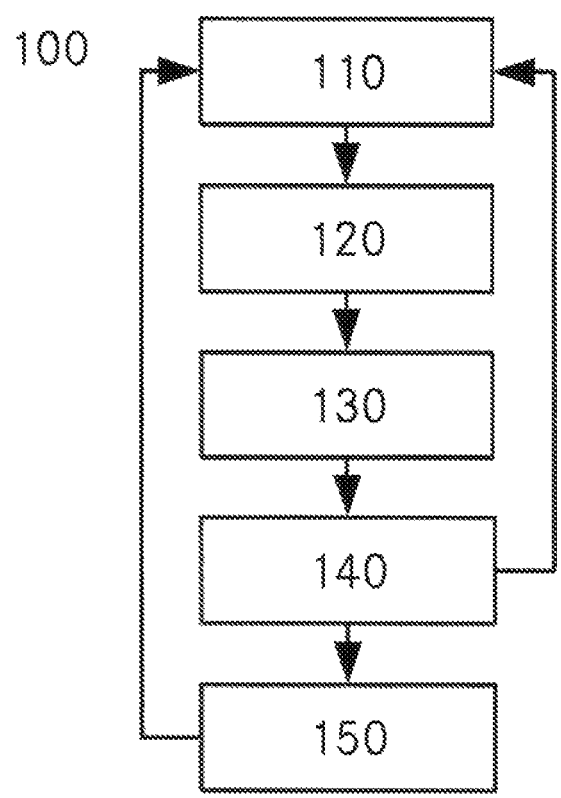
FIG. 1 shows a block diagram of a method embodiment for storing measured values.

FIG. 1 shows a block diagram 100 of an exemplary variant of a method for storing measured values. A first step 110 of the method comprises measurement for a physiological parameter, particularly on or in a human body. According to the method, the value measured in this manner is buffer-stored in a buffer store in a further step 120 of the method. In this case, the buffer store preferably comprises a number of registers in which a series of measured values can be buffer-stored and provided without any loss. In a subsequent step 130 of the method, the buffer-stored measured values are analyzed, with already stored values from a memory also being able to be included. The analysis 130 is used to perform variability analysis of the buffered measured values, in particular, and/or a trend analysis or an analysis of trend changes. In a further step 140, a relevance of a buffered measured value, for example of a most recently measured value, for the profile of the measurement curve is checked by generating a storage criterion and assigning it to a buffered measured value. The storage criterion is checked.

If the storage criterion is met, the buffer's measured value associated with the storage criterion is stored in a memory in a further step 150 of the method. In this case, it is also conceivable for a storage criterion to relate to a set comprising a plurality of measured values which are all stored when the criterion is met. The method then starts to ascertain a further measured value again in step 110.

If a storage criterion is not met, the method starts again in step 110 without performing the storage step 150. The measurement period used to repeat the method is chosen such that the profile of the physiological parameter is largely resolved.

Figure 2:
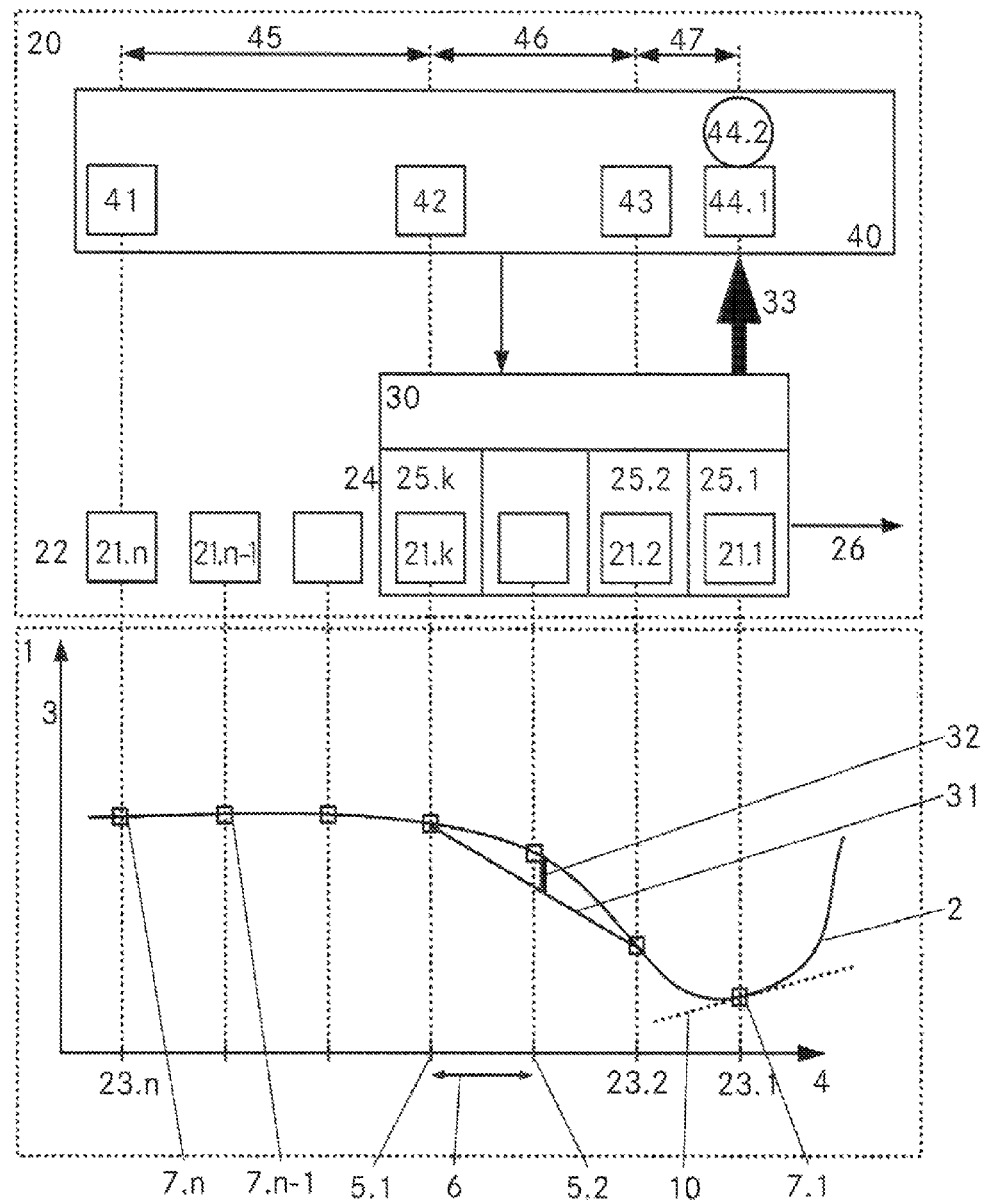
FIG. 2 shows a profile for a glucose concentration and a diagram for the storage method embodiment.

FIG. 2 shows a detail from a schematic graph 1 for a measured profile 2 of a physiological parameter, particularly a glucose concentration, for example in a human body. An ordinate 3 on the graph 1 shows the glucose concentration in arbitrary units, while the abscissa 4 shows the time advancing from left to right. Two successive scale lines 5.1 and 5.2 on the abscissa delimit a time interval which corresponds to a measurement period 6 which is used to continuously determine values 7.1 to 7.n for the curve profile 2. The values 7.1 to 7.n reproduce the profile 2 of the measured curve comparatively accurately.

In addition, FIG. 2 shows an abstracted diagram 20 of the components for processing, particularly storage, of the values 7 of the profile 2. In this case, the components shown are used to illustrate one variant of the method. The diagram 20 shows measured values 21.1 to 21.n measured by the method, which correspond to the measurements of the curve values 7.1 to 7.n, as abstract blocks of information for a series of measurements 22. In this case, the measured values 21 are arranged parallel to the time axis 4 of the graph 1 in line with their measurement time 23.1 to 23.n in a series.

When the method is carried out, a respective number of k measured values, in the present case the measured values 21.1 to 21.k, are stored in a buffer store 24 in order to allow access to at least one portion of already ascertained measured values 21.1 to 21.n. In this case, the buffer store 24 can operate on the basis of a known bucket-chain or FIFO principle. To this end, a number of registers 25.1 to 25.k are provided in the buffer store 24, the content of a last register 25.k being overwritten by the content of the penultimate register 25.k−1 when a new measured value 21.1 is ascertained afresh. This process is carried out over all the registers until a content of the register 25.2 has been overwritten by the content of the register 25.1. The freshly measured value 21.1 is then written to the first register 25.1. The buffer store 24 thus samples the entire series of measurements 22 in the form of a time window or measurement window essentially of length k measurement periods in the direction of advancing time 26 ("moving window").

When the method embodiment is carried out in line with FIG. 2, an evaluation apparatus 30 analyzes the measured values 21.1 to 21.k stored in the buffer 24 when required, with values 41 to 44 stored in a memory 30 also being able to be included. On the basis of the analysis, the evaluation apparatus 30 performs a check on one or more storage criteria, on the basis of which it is decided whether a measured value 21.1 in the buffer 24, in the present case a most recently measured value, needs to be stored in the memory 40. Such storage criteria may be firmly prescribed (firmly prescribed intervals of time) or, as in the case of the illustration in FIG. 2, can be determined adaptively on the basis of the current and previous curve profile 2. In line with the illustration in FIG. 2, the registers 25.1 to 25.k in the buffer 24 are accessed in the evaluation apparatus 30 in an evaluation step, and the measured values 21.1 to 21.k stored in said registers are analyzed and compared with the values 41 to 44 stored in the memory 40. The buffer-stored measured values 21.1 to 21.k or a subset thereof are used to determine a first derivative and also a second derivative of the curve profile 2 with respect to time. In addition, a combination of the buffered measured values 21.1 to 21.k and the stored values 41 to 44 is used for linear interpolation of the curve profile 2 in ranges.

In this case, a first storage criterion is deemed to have been met if the second derivative with respect to time exceeds a certain prescribed, value at the time 23.1 of a current measurement 21.1. This means that although the gradient 10 itself may be small, a curvature of the measurement curve 2 exceeds a certain value and is accordingly comparatively large. In this case, the current measured value 21.1 is stored, together with the instantaneous gradient 10 of the measurement curve 2, i.e. derivative with respect to time 10 at the time 23.1 of ascertainment of the measured value 21.1, in a memory 40 as a pair of values 44.1/44.2.

A second storage criterion is generated on the basis of a linear interpolation 31. In FIG. 2, the measured value 21.2 has been stored as a value 43 on the basis of the interpolation criterion, for example at an earlier time 23.2. At the time 232, the measured value, 21.2 represented the most recently measured value, and the most recently stored measured value 21.k is stored in the memory 40 as the stored value 42. Linear interpolation between the value 42 and the measured value 21.2 results in the line 31 shown. An interval between the interpolation 31 and the measurement curve 2, particularly a maximum for the interval, is used as a measure of error. In the present case, the measure of error or the interval 32 exceeded a prescribed value, which meant that the interpolation storage criterion was met for the measured value 21.2 and it was stored as stored value 43.

As becomes clear from FIG. 2, a variable interval of time for the stored values 41 to 44 is thus obtained. A first interval 45 between the successive stored values 41 and 42 is (n−k) times the measurement period 6, while an interval 46 between the stored values 42 and 43 is (k−2) times the measurement period 6. Between the last two stored values 43 and 44 there is an interval of time 47 of one measurement period 6.

As becomes clear from FIG. 2, three are fewer stored values in the memory 40 than in the whole of the continuously ascertained series of measurements 22. The measured values 21.k+1 to 21.n−1 and the measured values 21.3 to 21.k−1 have been singled out by the method, because they have comparatively little relevance for the curve profile 2, and have not been stored in the memory 40.

Whereas the example explained in FIG. 2 checks a plurality of storage criteria for a current measured value, certain method embodiments can also check only single storage criteria. In the present case, a combination has been chosen to illustrate the method more comprehensibly. In addition, it should be noted that a storage criterion can be assigned not necessarily to just a single measured value, such as a most recently measured value, but rather can also be assigned to a set of measured values which are stored or not stored on the basis of the storage criterion.

Figure 3:
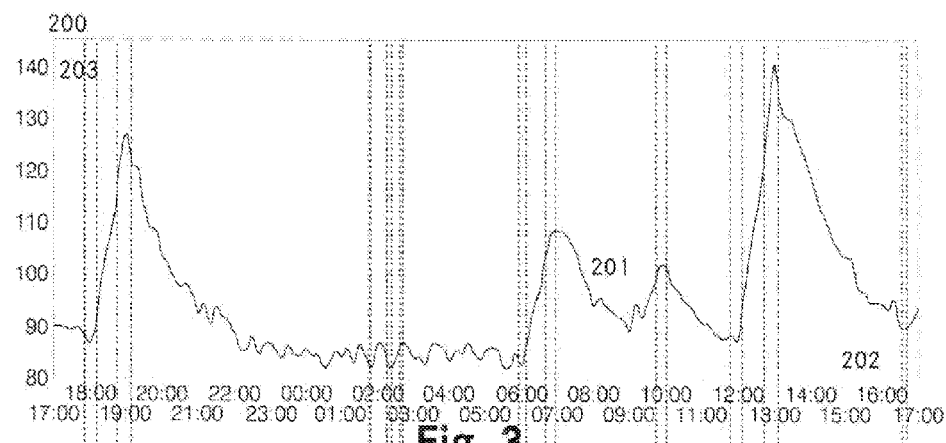
FIG. 3 shows a specific profile for a glucose concentration in a human over the course of 24 hours.

The graph 200 in FIG. 3 shows a simulated profile 201 for a glucose concentration in a person over the course of 24 hours. The abscissa 202 shows the time as a time of day from 17:00 on the first day to 17:00 on the next day. The ordinate 203 shows the glucose concentration in units of milligrams per deciliter. The range of values shown covers a: range from approximately 80 to approximately 140 units.

At about 17:00, the glucose concentration is in the region of approximately 90 units. At around 18:00, a dip in the blood's glucose concentration can be seen. A meal taken at about 18:00 raises the glucose level within about an hour essentially linearly to a local maximum value of approximately 128 units. Up to about 22:00, the glucose concentration falls largely exponentially to a minimum value of on average approximately 85. The glucose concentration fluctuates about this value until the next morning at 6:00 at low amplitude (approximately 3 units). A breakfast at about 6:00 raises the glucose level within the period of one hour, essentially linearly, to a value of approximately 110 units and subsequently reduces it, again largely exponentially, to a value of approximately 90 units by 9:00. A snack raises the glucose level, again essentially linearly, over the course of one hour to a value of approximately 102 units, whereupon it again falls largely exponentially to approximately 88 units at 12:00. A lunch taken at approximately 12:00 raises the glucose level within one hour essentially linearly to a maximum value of about 141 units, and the glucose level then falls largely exponentially to around 94 units at the end of the 24-hour profile shown. At about 16:30, there is a small dip in the glucose level 201 to approximately 90 units prior to this.

Figure 4:
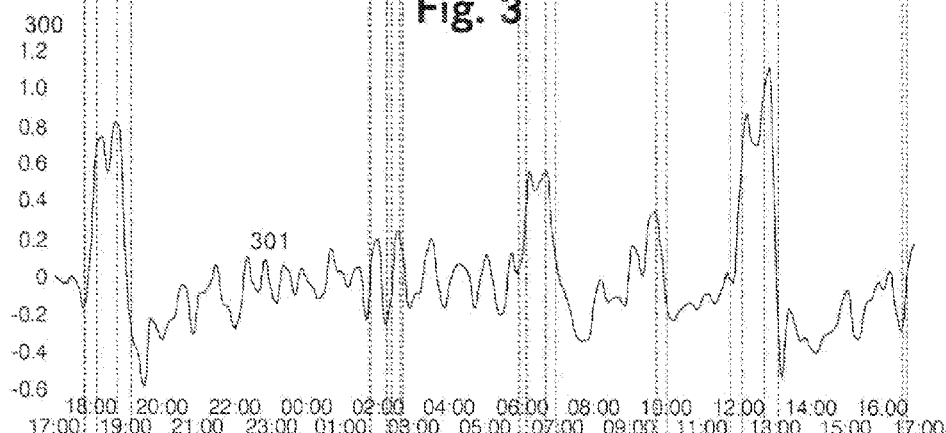
FIG. 4 shows a first derivative with respect to time of the glucose concentration profile in FIG. 3.
Figure 5:
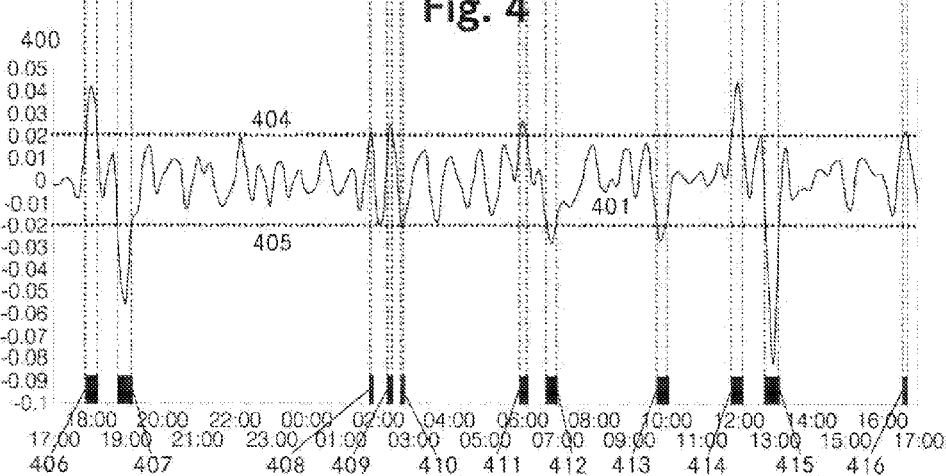
FIG. 5 shows a second derivative with respect to time of the glucose concentration profile in FIG. 3.

A graph 300 in FIG. 4 shows a derivative with respect to time 301 of the glucose concentration profile 201 shown in the graph 200 in FIG. 3, and a graph 400 shown in FIG. 5 shows a second derivative with respect to time 401 for the curve 201. In addition, the graph 400 in FIG. 5 shows a positive minimum value 404 and a negative absolute value minimum value 405 for the second derivative 401. The absolute values of the chosen minimum values 404 and 405 are purely illustrative in this case and may differ significantly in a specific implementation of the method. Time periods 406-416 in which the second derivative 401 exceeds the minimum values are shown in all three graphs 200, 300 and 400, but are particularly highlighted in FIG. 5 by blackened ranges.

A comparison of the position of the ranges 406 to 416 with the curve profile 201 in the graph 200 clearly shows that the second derivative of the glucose concentration profile with respect to time 201 is a criterion for detecting locations with a high level of change in the profile 201. By way of example, the range 406 denotes the position in time of the dip described above at about 18:00, while the position in time of the range 407 denotes the local maximum at about 19:00. Equally, corresponding large changes in the glucose concentration 201 can also be found for the ranges 411 and 412 (about 6:00 and 7:00), 413 (approximately 10:00), 414 and 415 (approximately 12:00 and 13:00) and for 416 (about 16:30). The ranges 408 to 410 relate to changes during the fluctuations at night around an essentially constant average which were described above.

In line with one variant of the method, pairs of values which firstly comprise the glucose value and secondly comprise the simultaneously ascertained first derivative with respect to time can be stored in the ranges 406 to 416. On the basis of such stored pairs of values, good knowledge can be obtained about the greatly changing profile of the glucose concentration 201 in the ranges 406 to 416. In particular, this can be used to reconstruct a profile 201 from the stored values with a high level of accuracy.

The second derivative, whose absolute value is comparatively small, in periods outside the ranges 406 to 416 means that no significant changes in the trend in the curve 201 are to be expected. In these ranges, the curve 201 can therefore be reconstructed retrospectively with a comparatively high level of accuracy on the basis of just a few stored values. In this case, it is in most cases sufficient to store the measured values without a first derivative or a trend, since no significant change in the curve gradient or in the trend is to be expected. In addition, in periods outside the ranges 406 to 416, the profile 201 exhibits, in a rough approximation, a behaviour which is largely known a priori (e.g. a linear rise, an exponential fall) and which can likewise be included in the method.

Figure 6:
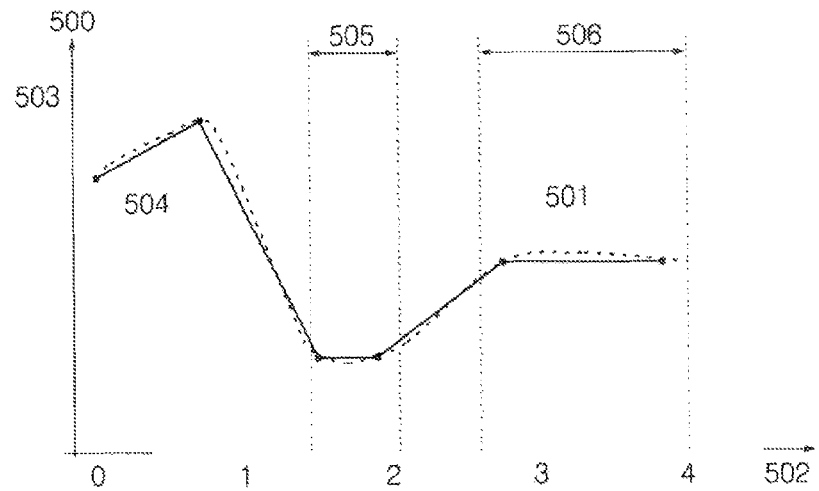
FIG. 6 shows a profile for a glucose concentration over 4 hours.

FIG. 6 shows a schematic profile 501 of a measured glucose concentration over four hours. A graph 500 which is shown has an abscissa 502 and an ordinate 503, the abscissa 502 showing the time as it advances and the ordinate 503 showing the glucose concentration. In this case, the measured profile 501 is shown in dashes, while a reconstructed profile 504 is indicated by six stored values which are linearly interpolated. Table 1 below indicates the reduction in the storage rate, as achieved by the method, in comparison with complete storage of the whole series of measurements over four hours (last row, one-minute interval). In this case, the profile 501 has periods 505 and 506 of low dynamics, and high dynamics otherwise. The second column of Table 1 indicates the storage mode: mode 1 for storage intervals of variable length (e.g.

adaptively adjusted to the profile of the measurement curve or stipulated on the basis of a priori knowledge about the measurement curve) and mode 2 for storage intervals of constant length. Whereas the methods in examples A-B and D-F use only a single one of the two storage modes both modes are used in example C. In this case, particular use is made of a priori knowledge about the future profile of the glucose concentration for stipulating time ranges in which either storage mode 1 or storage mode 2 is used. In ranges in which dynamics are probably high (e.g. the taking of meals), a fixed measurement interval of five minutes is prescribed (storage mode 2) in order to ensure good sampling of the concentration profile. In ranges in which dynamics are probably low or absent (e.g. at night); it is sufficient to ascertain measured values only sporadically at variable intervals of time, in example C one measured value per zero-dynamics time interval, since the glucose level does not change significantly in these periods.

In other variants of the method, it is possible to change over between storage modes on the basis of a variability analysis for the measurement curve, for example. By way of example, as soon as high dynamics are established, the method uses storage mode 2, and detection of low dynamics prompts the use of storage mode 1. Alternatively, it may be advantageous to use storage mode 1 in ranges, of high dynamics, and similarly to use storage mode 2 in ranges of comparatively low to absent dynamics.

TABLE 1

Reduction in Storage Volume by the Storage Method

| No. | Mode | Storage Criterion | Stored Values | Reduction |
|---|---|---|---|---|
| A | 1 | lin. interpolation trend information | 6 measured values 6 time values | 95.0% |
| B | 1 | lin. interpolation trend information | 6 measured values 6 trend values 6 time values | 92.5% |
| C | 1 + 2 | lin. interpolation a priori knowledge about profile | 24 measured values (5-min. interval for dynamics) 2 measured values 2 time values (no dynamics) | 88.0% |
| D | 2 | 15-min. interval | 16 measured values | 87.0% |
| E | 2 | 5-min. interval | 48 measured values | 80.0% |
| F | 2 | 1-min. interval | 240 measured values | 0.0% |

Figure 7:
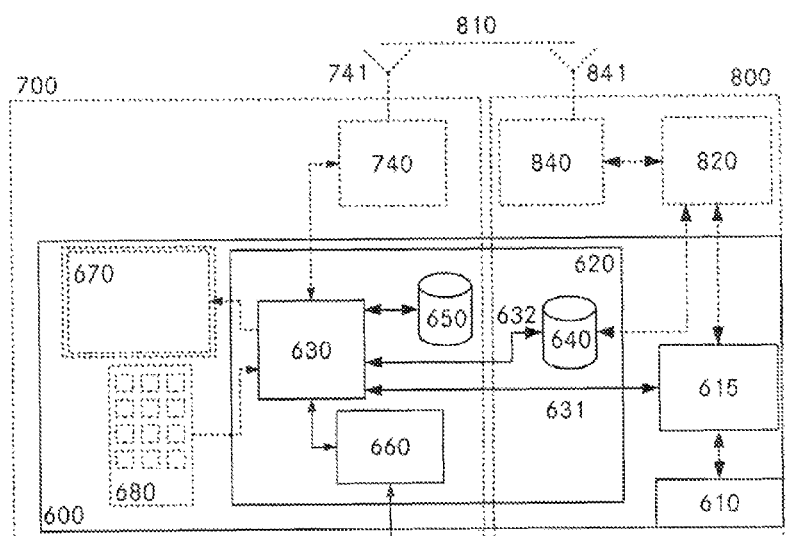
FIG. 7 shows an apparatus for carrying out a method embodiment.

FIG. 7 shows a schematic view of an appliance 600 for processing and storing a series of measured values for a time-dependent parameter which is measured in or on a human body, particularly a glucose concentration in a body fluid such as blood. In this case, the arrangement comprises a glucose sensor 610 and a processing unit or a system controller 620. In the example shown, the glucose sensor 610, for example as an enzymatic sensor, electrochemically (or else photometrically) measures the glucose concentration in a body fluid. Alternatively, the glucose sensor 610 used may be affinity sensors, which are evaluated optically (that is to say also by photometrics) or else fluidically (viscosity measurement or osmotically, or other fluidic parameters).

In line with the example shown, the system controller 620 comprises a central processing unit 630 (CPU) and a buffer, store 640 and a memory 650. By way of example, an interface 660 on the system controller 620 allows the appliance 600 to be connected to external peripheral devices such as data processing installations, e.g. personal computers (PC), belonging to a patient or belonging to a person responsible for the health of the patient, or else allows it to be connected to an external insulin release apparatus, to Personal Digital Assistants (PDAs) or to mobile phones for remote data transmission, for example.

In the example shown, the measurement sensor 610 is connected to an analogue electronics section 615 which converts the sensor signal from the measurement sensor 610 and makes it available to the central processing unit 630. The CPU 630 is connected to the analogue electronics section 615 by means of a line 631 and to the buffer store 640 by means of a line 632. In addition, the CPU 630 has connections to the memory 650 and to the interface 660. In this arrangement, the CPU 630 controls the sensor 610 and periodically stores a measured glucose value in the buffer store 640 using a measurement period. When certain versions of the method are carried out, the CPU 630 removes measured values from the buffer store 640, determines storage criteria and stores measured values for which a storage criterion is met in the memory 650.

In this case, display means, e.g. in the form of a graphical display 670, and control elements, for example in the form of a keypad 680, may additionally be provided, the display 670 allowing graphical presentation of values stored in the memory 650, and the keypad 680 allowing interaction with the appliance 600. By way of example, the keypad 680 can be used to change a display mode of the display 670 or else to take action in certain versions of the method which is being carried out on the CPU 630, for example by changing a storage mode.

In one modification of the illustrated embodiment of the appliance 600, an apparatus comprises a control unit and a measurement unit connected thereto, which are each in the form of a standalone appliance 700 (control unit) or 800 (measurement unit). The measurement unit 800 is connected to the control unit 700 by means of a wireless RF link 810. It goes without saying that a wireless link could also be set up using optical, acoustic, electrostatic (capacitive) and/or inductive methods, for example. In other embodiments, the measurement unit and the control unit may also be connected to one another by wire. The wireless RF link 810 described is therefore one specific variant of possible embodiments with separate measurement and control units.

The control unit 700 comprises the CPU 630, the memory 650 and the interface 660, and, as for the appliance 600, the display 670 and/or the keypad 680 may optionally be present. In line with the integrated embodiment of the appliance 600, these components are connected to one another. In addition, the control unit 700 has an interface 740 with an antenna 741 for receiving and also for sending RF signals.

The measurement unit 800 comprises the buffer store 640 for buffer-storing measured values which are picked up by the sensor 610, which the measurement unit 800 likewise comprises. The measurement unit 800 can have a dedicated central processing unit (CPU) 820 which is connected to the buffer store 640 and also to the analogue electronics section 615 which is likewise provided in the measurement unit 800. In this case, the analogue electronics section 615 is connected to the glucose sensor 610 and makes its converted sensor signals available to the CPU 820. In addition, the measurement unit 800 comprises an interface 840 with an antenna 841 for the purpose of data transmission. The CPU 820 controls the sensor 610 such that measured values are periodically buffer-stored in the buffer store 640.

In contrast to the integrated appliance 600, the CPU 630 in the illustrated embodiment of the apparatus with a separate control unit 700 and measurement unit does not have a direct connection to the buffer store 640 and to the sensor 610 in the measurement unit 800. Data from the measurement unit 800 and its components are transmitted or sent to the control unit 700 exclusively via the wireless RF link 810. In this case, the wireless RF link 810 may be in bidirectional form or else allow data transmission from the measurement unit 800 to the control unit 700 only, depending on requirements.

The measured values stored in the buffer store 640 are preferably transmitted to the control unit 700: at periodic intervals. To this end, the measured values in the buffer store 640 are read by the CPU 820 and transmitted to the interface 840, are encrypted therein, for example, and are transmitted from the interface 840 to the control: unit 700 via the wireless link 810 using the antenna 841.

The RF signal 810 from the measurement unit 800 is received by means of the antenna 741 of the control unit 700 and is processed further, for example decrypted, by the interface 740. The received measured values are then transmitted from the interface 740 to the CPU 630, which, in line with certain versions of the method stores selected measured values in the memory 650. Upon appropriate request, for example by an external data processing installation or on the basis of an input by a user, the CPU 630 can remove the stored values from the memory 650 and forward them to the interface 660 and/or display them on the display 670, for example.

The integrated appliance 600 has the advantage that it need only have one CPU 630 and the CPU 630 can be connected to the sensor 610 and to the buffer store 640 directly by means of lines 670 and 680. In this case, however, all the necessary components need to be accommodated in a single appliance, which can be comparatively unwieldy. In contrast, an embodiment with separate units 700 and 800 allows a comparatively small and inconspicuous form for the measurement unit 800, which can be fitted on the body independently of the control unit 800, in particular. By way of example, the control unit 700 can in this case be carried inconspicuously in a coat or trouser pocket. However, this requires additional components such as interfaces 740 and 840 for communication and an additional CPU 820 in the measurement unit 800.

In summary, it can be stated that method embodiments allow selective storage with a comparatively high level of accuracy in ranges with unexpected changes, i.e. in ranges with large trend changes, while only comparatively few values are stored in ranges with a small trend change and hence an easily predicted profile. Nevertheless, the total quantity of the values stored on the basis of the method, which may result in a significantly smaller volume of data, as a complete series of measurements can be used to reconstruct the original profile of the measurement curve with good accuracy. In addition, the selective storage of measured values makes it a simple matter to filter out noise and other undesirable fluctuations in the measured values. Furthermore, to reduce data further, it is firstly not a problem to include a priori knowledge of the expected profile of the measurement curve in the method, and secondly the method is also adaptive such that it can adjust a storage mode or storage intervals between values which are to be stored to suit the current profile of the measurement curve.

Thus, embodiments of the method for storing a series of measurement are disclosed. One skilled in the art will appreciate that the teachings can be practiced with embodiments other than those disclosed. The disclosed embodiments are presented for purposes of illustration and not limitation, and the invention is only limited by the claims that follow.

What is claimed is:

1. A method for improving storage of an apparatus that stores a series of measured values which represent a time-dependent parameter measured in or on the human body by a sensor, comprising:

providing an apparatus for storing the series of measured values, the apparatus comprising a system controller having a memory and a first storage mode in which an interval of time between each successively stored measured value is variable based on automatic selection of the time interval by the system controller using a storage criterion determined from information on at least one event which influenced the time-dependent parameter;

measuring by the sensor a first number of measured values in a series; and storing in the memory by the system controller a second number of measured values in the series of measured values as measured data using the first storage mode, wherein the second number is smaller than the first number which reduces a stored volume of the measured data in the memory of the apparatus needed to reproduce a profile based on the time-dependent parameter from the measured data.

2. The method according to claim 1, wherein the first storage mode the interval of time is adjusted on the basis of a time-based variability of the measured values.

3. The method according to claim 2, wherein a measure of error in an interpolation between a last stored value and a most recently measured value is formed for a relevant range of the series of measured values, wherein a value from the relevant range of the series is stored if the measure of error exceeds a certain maximum value.

4. The method according to claim 3, wherein linear interpolation is performed between the last stored value and the most recently measured value.

5. The method according to claim 1, further comprising a second storage mode in which the interval of time between each successively stored value is constant, wherein particularly the first storage mode is used if a variability of the measured values is below a prescribed value, and the second storage mode is used if the variability exceeds the prescribed value.

6. The method according to claim 1, wherein trend values are ascertained from the series of measured values.

7. The method according to claim 6, wherein a Kalman filter is used to ascertain the trend values.

8. The method according to claim 1, wherein a current measured value is stored if a trend value change associated with the currently measured value exceeds a prescribed minimum value.

9. The method according to claim 6, wherein a current measured value is stored if a trend value change associated with the currently measured value exceeds a prescribed minimum value.

10. The method according to claim 6, wherein trend values are also stored besides the stored values.

11. The method according to claim 10, wherein trend change values corresponding to a second derivative of the measured values are ascertained from the series of measured values.

12. The method according to claim 10, wherein time-based interpolation points are provided, at which the relevant trend value and/or trend change value, but not the measured value itself, is stored.

13. The method according to claim 1, wherein the time-dependent parameter measured in or on the human body is a physiological glucose concentration.

14. The method according to claim 1, wherein the at least one event which influenced the time-dependent parameter is selected from an analyses of the measured values or values derived therefrom, a discrepancy or error value in the measured values from a prediction or extrapolation, fluctuations based on time scale, noise, or appliance-related short-term measurement inaccuracies, time of day, carbohydrate content of meals taken, administered insulin boluses, nature and duration of an undertaken activity, fasting state, and sleeping state.

15. A method for improving storage of an apparatus that stores a series of measured time-dependent glucose values from a continuous glucose monitor while permitting retrospective reconstruction of measured data with sufficient accuracy, comprising:
provided an apparatus for storing the series of measured values, the apparatus comprising a system controller having a memory and a first storage mode in which an interval of time between each successively stored measured value is variable based on automatic selection of the time interval by the system controller using a storage criterion determined from information on at least one event which influenced the time-dependent parameter, and the apparatus comprising a second storage mode;
measuring a first number of glucose values in a series by a continuous glucose monitor;
analyzing by the system controller whether the first number of glucose values is below or above a prescribed value;
using by the system controller the first storage mode that is adaptive if the first number of glucose values is below the prescribed threshold to store in the memory of the apparatus a second number of glucose values with the interval of time between each successively stored value being variable and the second number of glucose values being smaller than the first number which reduces a stored volume of measured data in the memory of the apparatus;
using by the system controller the second storage mode that is constant if the first number of glucose values is above the prescribed threshold to store in the memory of the apparatus the second number of glucose values with the interval of time between each successively stored value being constant and the second number of glucose values being smaller than the first number which further reduces the stored volume of the measured data in the memory of the apparatus; and,
storing in the memory of the apparatus by the system controller trend values with the second number of glucose values to improve reconstruction of the first number of glucose values from the stored volume of the measured data for a measurement curve.

16. An apparatus for storing a series of measured values which represent a time-dependent parameter measured in or on the human body, comprising:
a measuring apparatus which continuously measures and feeds in a series of measured values for a parameter measured on, or in a human body, wherein the parameter is a glucose concentration;
a system controller having a memory unit for storing the measured values,
wherein the system controller is programmed such that, for a first number of the values covered by the series, a second number of values are stored in memory by the system controller as measured data using a first storage mode of the apparatus in which an interval of time between each successively stored measured value is variable based on automatic selection of the time interval by the apparatus using a storage criterion determined from information on at least one event which influenced the time-dependent parameter, and
wherein the second number is smaller than the first number which reduces a stored volume of the measured data in the memory of the apparatus needed to reproduce a profile based on the time-dependent parameter from the measured data.

17. The apparatus according to claim 16, wherein a buffer store is provided which can be used to buffer-store continuously measured values, and also an evaluation apparatus for analyzing a variability of the measured values is present.

18. The apparatus according to claim 16, wherein the system controller calculates at least one of trend values using an expected future profile of the measured parameter, a derivative of the measured values with respect to time, and a derivative of the trend values with respect to time.

19. The apparatus according to claim 16, wherein the apparatus is a portable apparatus.

20. A computer program product embodied on a tangible computer readable medium comprising instructions that when executed on an apparatus having a system controller and memory cause the apparatus to:
a) receive by the system controller a first number of the values covered by a series of measured values which represent a time-dependent parameter measured in or on a human body by a measuring apparatus in communication with the apparatus, and
b) store in memory by the system controller a second number of values covered by the series as measured data using a first storage mode of the apparatus in which an interval of time between each successively stored measured value is variable based on automatic selection of the time interval by the system controller using a storage criterion determined from information on at least one event which influenced the time-dependent parameter, wherein the second number is smaller than the first number which reduces a stored volume of the measured data in the memory of the apparatus needed to reproduce a profile based on the time-dependent parameter from the measured data.

21. The computer program product according to claim 20, further comprising instructions that when executed on the apparatus having the system controller and memory cause the apparatus to:
c) store in a buffer continuously measured values received by the system controller, and analyze the measured values by the system controller for variability.

22. The computer program product according to claim 20, further comprising instructions that when executed on the apparatus having the system controller and memory cause the apparatus to:
d) calculate trend values using an expected future profile of the measured parameter.

23. The computer program product according to claim 20, wherein the instructions cause the apparatus to calculate the trend values using the expected future profile of the measured parameter by causing the system controller to calculate a derivative of the measured values with respect to time and to determine a derivative of the trend values with respect to time.

* * * * *

UNITED STATES PATENT AND TRADEMARK OFFICE
CERTIFICATE OF CORRECTION

| | | |
|---|---|---|
| PATENT NO. | : 9,014,986 B2 | Page 1 of 1 |
| APPLICATION NO. | : 12/760808 | |
| DATED | : April 21, 2015 | |
| INVENTOR(S) | : Michael Krieftewirth | |

It is certified that error appears in the above-identified patent and that said Letters Patent is hereby corrected as shown below:

Specification

Col. 2, Line 54,
"advantageous to store additional values, for examples values" should read
--advantageous to store additional values, for example values--;

Col. 11, Line 23,
"As becomes clear from FIG. 2, three are fewer stored" should read
--As becomes clear from FIG. 2, there are fewer stored--;

Col. 11, Line 45,
"per deciliter. The range of values shown covers a: range from" should read
--per deciliter. The range of values shown covers a range from--;

Col. 15, Line 7,
"preferably transmitted to the control unit 700: at periodic" should read
--preferably transmitted to the control unit 700 at periodic--;

Col. 15, Line 11,
"from the interface 840 to the control: unit 700 via the wireless" should read
--from the interface 840 to the control unit 700 via the wireless--; and Col. 15, Line 58,
"measurement are disclosed. One skilled in the art will appre-" should read
--measurements are disclosed. One skilled in the art will appre- --.

Signed and Sealed this
First Day of March, 2016

Michelle K. Lee
*Director of the United States Patent and Trademark Office*